(12) United States Patent
Bunke et al.

(10) Patent No.: US 7,317,402 B2
(45) Date of Patent: Jan. 8, 2008

(54) ALARM IN A DEVICE FOR DISPENSING VOLATILE ANESTHETICS

(75) Inventors: Claus Bunke, Sereetz (DE); Jürgen Müller, Lübeck (DE); Matthias Witt, Bad Schwartau (DE); Sven Heyer, Lübeck (DE); Michael Heidschmidt, Lübeck (DE); Martin Wunderlich, Lübeck (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 196 days.

(21) Appl. No.: 11/176,118

(22) Filed: Jul. 7, 2005

(65) Prior Publication Data

US 2006/0087441 A1 Apr. 27, 2006

(30) Foreign Application Priority Data

Sep. 25, 2004 (DE) .................... 10 2004 046 644

(51) Int. Cl.
*G08B 21/00* (2006.01)

(52) U.S. Cl. .................. 340/679; 340/686.1; 340/606; 340/662; 340/663; 137/455; 137/551; 600/301

(58) Field of Classification Search ............... 340/679, 340/686.1, 606, 662, 663; 137/455, 551; 600/301; 300/301
See application file for complete search history.

(56) References Cited

U.S. PATENT DOCUMENTS 4,345,612 A * 8/1982 Koni et al. ............ 137/101.19

* cited by examiner

*Primary Examiner*—Tai Nguyen
(74) *Attorney, Agent, or Firm*—McGlew and Tuttle, P.C.

(57) ABSTRACT

An alarm is associated with a device for dispensing volatile anesthetics. The alarm and device is designed such that an alarm is triggered whenever the operating voltage is interrupted and an assembly unit that determines the dispensing of at least one anesthetic is not in a prescribed state of operation.

20 Claims, 2 Drawing Sheets

ALARM IN A DEVICE FOR DISPENSING VOLATILE ANESTHETICS

CROSS REFERENCE TO RELATED APPLICATIONS

This application claims the benefit of priority under 35 U.S.C. § 119 of German Application DE 10 2004 046 644.0 filed Sep. 25, 2004, the entire contents of which are incorporated herein by reference.

FIELD OF THE INVENTION

The present invention pertains to an alarm in a device for dispensing volatile anesthetics, which triggers an alarm when the dispensing device is not ready for dispensing without the presence of an intended operating voltage, i.e., when there is a risk for dispensing an insufficient quantity.

BACKGROUND OF THE INVENTION

The present invention can be used in an alarm control for an apparatus for dispensing volatile anesthetics, also called vapors, which said apparatus is controlled by means of a handwheel where dispensing, which cannot be guaranteed as a consequence of the lack of operating voltage, must be prevented from being set with the handwheel when the apparatus is switched off or in case of failure of the operating voltage.

Electricity, which is taken from a supply network, is usually necessary for the operation of an anesthetic dispensing apparatus. The dispensing proper is carried out by means of a mechanically adjustable assembly unit with variable flow cross section. The dispensing operation is controlled, monitored and secured by various electronic assembly units during normal operation. Critical states of operation are avoided or displayed by software-assisted warnings or alarm reports. Some of the functions intended for this are dispensable when the apparatus is put out of operation.

However, if the apparatus is not ready to operate, for example, because of the energy supply being interrupted or switched off, the user must be alerted about this at least when there is a risk for no dispensing or dispensing of an insufficient quantity of anesthetics. This function must not depend on the supply of the operating voltage via the supply network or the functioning of the software.

In case of conventional anesthetic dispensers with handwheel, securing against the incorrect dispensing or dispensing of an insufficient quantity of anesthetics is achieved by the handwheel for setting the dispensing concentration being locked in the zero position when the operating voltage from the supply network fails. It is thus impossible to set a dispensing concentration with the energy supply switched off when the handwheel was in the zero position at the time of interruption of the operating voltage.

However, this locking only becomes active in the zero position of the handwheel. However, if the energy supply fails at another concentration setting, an acoustic alarm of a limited duration in time is triggered, but the concentration setting continues to be able to be changed. The locking of the handwheel is subject, moreover, to mechanical wear and may be damaged by forcibly rotating the locking handwheel.

SUMMARY OF THE INVENTION

The object of the present invention is to provide security, in case of interruption of the operating voltage of a device for dispensing liquid anesthetics, against incorrect dispensing or dispensing of an insufficient quantity of anesthetics from the dispensing device, which functions independently from the state of operation of the dispensing device at the time of the interruption of the operating voltage and is subject to slight wear at best.

According to the invention, an alarm in a device for dispensing volatile anesthetics is provided. The alarm is designed such that an alarm is triggered whenever the operating voltage is interrupted and an assembly unit, that determines the dispensing of at least one anesthetic, is not in a prescribed state of operation.

The present invention is based on the fact that, in addition to the software-driven alarm control in a dispensing device for volatile anesthetics, an additional possibility of triggering an alarm is provided, which triggers an alarm independently from the functioning of the software or the provision of the operating voltage via the supply network as soon as there is a risk for incorrect dispensing or dispensing of an insufficient quantity of anesthetics. This alarm triggering advantageously takes place via the same acoustic signal transmitter as a software-controlled alarm triggering during normal operation.

The present invention comprises an alarm in a device for dispensing volatile anesthetics, which is designed such that an alarm is triggered whenever the operating voltage is interrupted and an assembly unit that determines the dispensing of at least one anesthetic is not in a prescribed state of operation.

It can be used especially when an assembly unit that determines the dispensing of at least one anesthetic comprises a mechanism with variable flow cross section, whose flow cross section can be set by means of a handwheel. This is the case, for example, with vapors.

The present invention can also be used advantageously when an assembly unit that determines the dispensing of at least one anesthetic comprises an electronically driven valve assembly unit. In an advantageous embodiment, at least one electronically driven valve assembly unit may be combined with a mechanism with variable flow cross section, whose flow cross section can be set by means of a handwheel.

The prescribed state of operation, in which no alarm is triggered in case of interruption of the operating voltage from the supply network, may be the closed state of the mechanism with variable flow cross section, in which the handwheel is in a zero position.

As an alternative, the prescribed state of operation, in which no alarm is triggered in case of interruption of the operating voltage from the supply network, may be a state of the mechanism with variable flow cross section in which the flow cross section is below a threshold value.

The position of the handwheel can be evaluated as the indicator of the state of operation of the mechanical assembly unit in both cases. In case of failure of the operating voltage from the supply network, the energy for the alarm that may become necessary is taken from a buffer source, preferably a rechargeable battery.

This can be advantageously embodied when at least one switch is contained, which is actuated by the handwheel and is in the open state when the handwheel is in a position in which no alarm is to be triggered, and which is in the closed state when the handwheel is in a position in which an alarm is to be triggered, and which is integrated in a current path that connects the alarm-triggering component with the output voltage of a buffer source only when the operating voltage from the supply network is interrupted. Such a current path may lead, for example, via at least one semiconductor element that is not conductive when the operating voltage is present. The output voltage of the buffer source can be present at the alarm-triggering component only when the semiconductor component becomes conductive and when the switch at the handwheel is additionally closed. An alarm can thus be triggered independently from the software. Furthermore, it is advantageous if no current is taken from the buffer source when the anesthetic dispenser is switched off and the handwheel is in the zero position.

An additional locking may be dispensed with due to the software-independent alarm control, because the user is alerted by an acoustic alarm, whose duration in time is limited only by the capacity of the buffer source, when the handwheel is opened that the apparatus for dispensing anesthetics is not ready to operate. Moreover, the same behavior is always obtained regardless of the concentration that was set on the handwheel at the time of the interruption of the operating voltage from the supply network.

In case of failure of the energy supply during the dispensing, the user is prompted by the permanent alarm to turn the handwheel into the zero position, which is necessary for the proper restart of the device.

The present invention will be explained in greater detail on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiments of the invention is illustrated.

DESCRIPTION OF THE PREFERRED EMBODIMENTS

Figure 1:
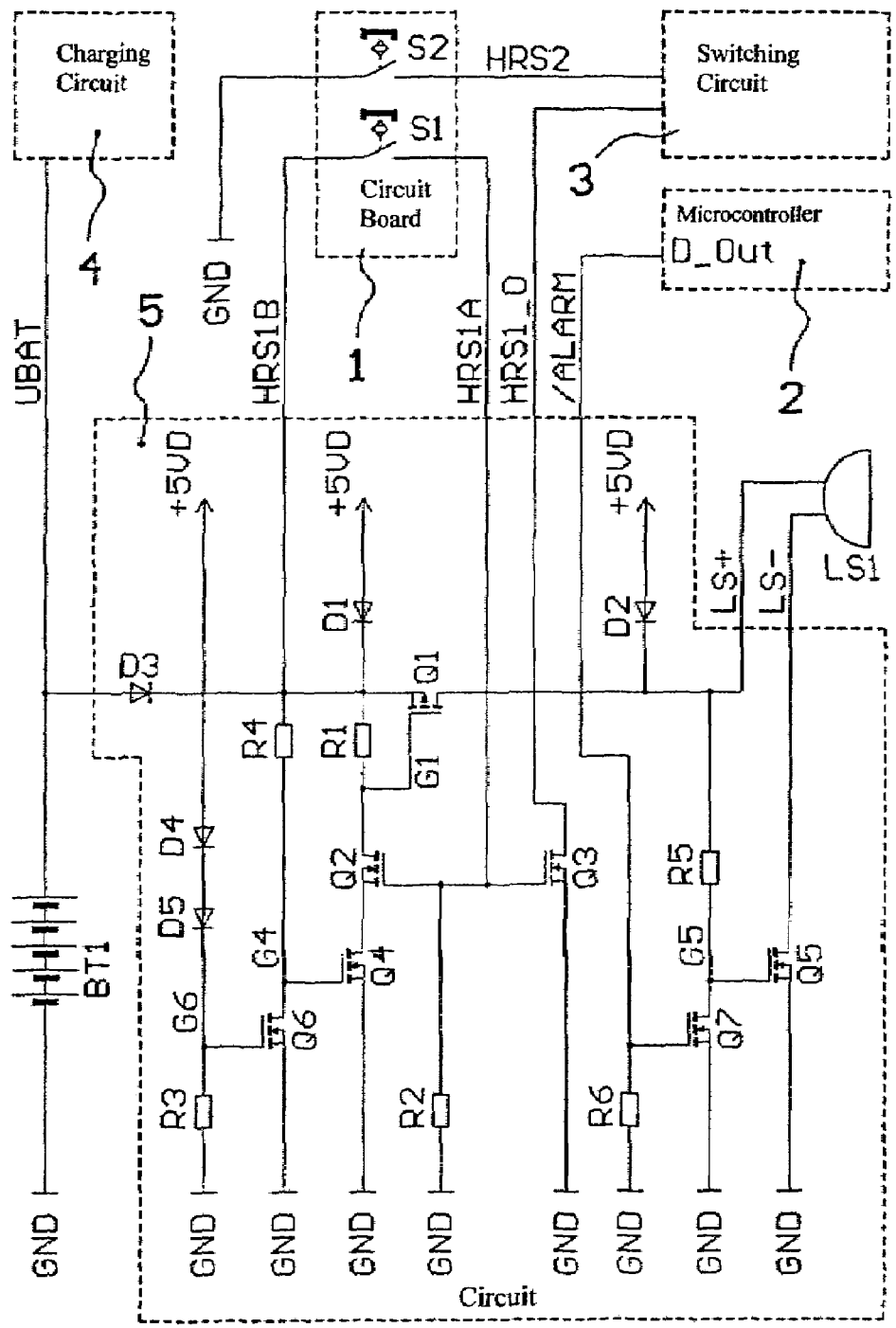
FIG. 1 is a circuit diagram of a device according to the present invention for triggering an alarm in a device for dispensing volatile anesthetics and the connection thereof to peripheral assembly units.

Referring to the drawings in particular, a printed circuit board 1 is arranged under the handwheel 20 for setting the dispensing concentration and carries two Reed switches S1 and S2. These are opened below a minimum concentration setting and are otherwise closed. The minimum concentration setting may also be a possibly mechanically supported zero position 22. The switching states are evaluated during normal operation by the software of a microcontroller 2. A switching circuit or switch debouncer 3 (that monitors switches and provides a switch change-of-state output, simplifying microprocessor (µP) or the microcontroller 2 polling and interrupts, for example, a MAX6818 is provided for processing the signals. S1 and S2 are advantageously designed as a redundant pair of switches.

A rechargeable battery BT1 is charged as needed during the normal operation by a charging circuit 4. Furthermore, an acoustic signal transmitter LS1 is present, which is controlled by the microcontroller 2 during the normal operation. The above-mentioned elements are connected with one another by a circuit 5, which ensures that only output signals of the microcontroller 2 can lead to triggering of the acoustic signal transmitter LS1 in the presence of the prescribed operating voltage from the supply network, whereas a closed switch S1 always leads to the triggering of an alarm due to the triggering of the acoustic signal transmitter LS1 in case of interruption of the operating voltage.

The mode of operation of the circuit in the presence and interruption of the operating voltage from the supply network will be explained below.

The operating voltage +5 VD from the supply network is present during normal operation. This is in a voltage range from +4.75 V to +5.5 V, and the microcontroller 2 is active. No software-independent alarm must be triggered on opening the handwheel. This is ensured as follows: Current is flowing into the resistor R3 via the two diodes D4 and D5. As a result, a voltage of about 3.6 V becomes established at the gate G6 of the N-channel MOSFET Q6, and the drain-source section of Q6 becomes conductive. As a result, a voltage of approx. 0 V becomes established at the gate G4 of the N-channel MOSFET Q4, so that the drain-source section thereof is blocked.

The gates of the two MOSFETs Q2 and Q3 are maintained at a voltage of 0 V via the resistor R2 with the handwheel switch S1 opened, so that Q2 and Q3 are blocked as well.

If the handwheel switch S1 closes, the voltage increases at the gates of Q2 and Q3 and both MOSFETs become conductive. Q3 passes on the switching state of S1 to the debouncer circuit 3. No current can flow over the drain-source section of Q2, because Q4 is blocked. Thus, no current is flowing over the resistor R1, either, the gate-source voltage of the P-channel MOSFET Q1 is zero, and Q1 is blocked.

To make it possible to transmit the switching state of S1 to the debouncer circuit 3, it is necessary for the signal HRS1B to carry a voltage that is sufficient for the energizing of Q3. This voltage is provided either from the rechargeable battery BT1 via the diode D3 or from the +5 VD operating voltage via D1.

The signal line LS+ always carries a voltage of about +4.3 V during normal operation. This is the positive supply voltage for the signal transmitter LS1. The microcontroller 2 controls the alarm via the digital signal, which is provided via D_Out and is present above the resistor R6 at the gate of the N-channel MOSFET Q7.

If this signal has a high level, i.e., about +5 V, then Q7 is conductive and Q5 is blocked, because its gate G5 is grounded. As a result, no current can flow through the signal transmitter LS1.

If D_Out carries a low level, i.e., about 0 V, then Q7 is blocked and Q5 is conductive. The signal transmitter LS1 is energized and an acoustic alarm is triggered.

In the switched-off state or with the operating voltage from the supply network interrupted, the voltage on +5 VD is about 0 V. The microcontroller is not operating and the control output D_Out has high ohmic resistance. The gate of Q7 is maintained at a low level in a defined manner via the resistor R6, so that Q7 is blocked.

The HRS1B signal is set at a voltage of about 6 V via the diode D3, which approximately corresponds to the output voltage of the rechargeable battery BT1. At the same time, D1 prevents current from being able to flow from the battery into +5 VD and to put the electronic control unit into operation.

The gate G6 of Q6 is maintained at 0 V in a defined manner via R3. Thus, Q6 remains blocked and Q4 is energized via R4. The gate of Q2 (HRS1A signal) is maintained at 0 V in a defined manner via R2 when the handwheel switch S1 is opened, i.e., when the handwheel is in the zero position, so that Q2 is blocked. Thus, no current is flowing over the resistor R1, the gate source voltage of Q1 is zero, and Q1 is blocked as well. The voltage on the signal LS+is approx. 0 V.

Since MOSFETs do not take up any control current in case of static triggering, no appreciable current is taken from the battery with the handwheel switch opened.

If the handwheel switch S1 is closed, the voltage on the HRS1A signal increases to approx. 6 V. As a result, the two MOSFETs Q2 and Q3 are energized.

Due to its electric insulation between the gate and the drain-source section, Q3 prevents current from being able to flow into the input of the debouncer circuit 3.

Due to Q2 being energized, current flows through R1, as a result of which a voltage drops over R1, and this voltage will now also cause the P-channel MOSFET Q1 to become conductive. Its gate-source voltage is approx. −6 V in this state. Current flows via Q3 and Q1 from the rechargeable battery BT1 to the signal transmitter LS1. The LS+signal now carries a voltage of approx. 6 V. Since Q7 is blocked, Q5 is energized via the resistor R5 and current is sent to the signal transmitter LS1. Thus, an acoustic alarm is always triggered in the absence of an operating voltage from the supply network if the switch S1 is closed. It can thus be guaranteed by a corresponding linking of the switch S1 with the handwheel that the alarm will always be triggered when the handwheel is outside the zero position or outside a set range of positions.

Figure 2:
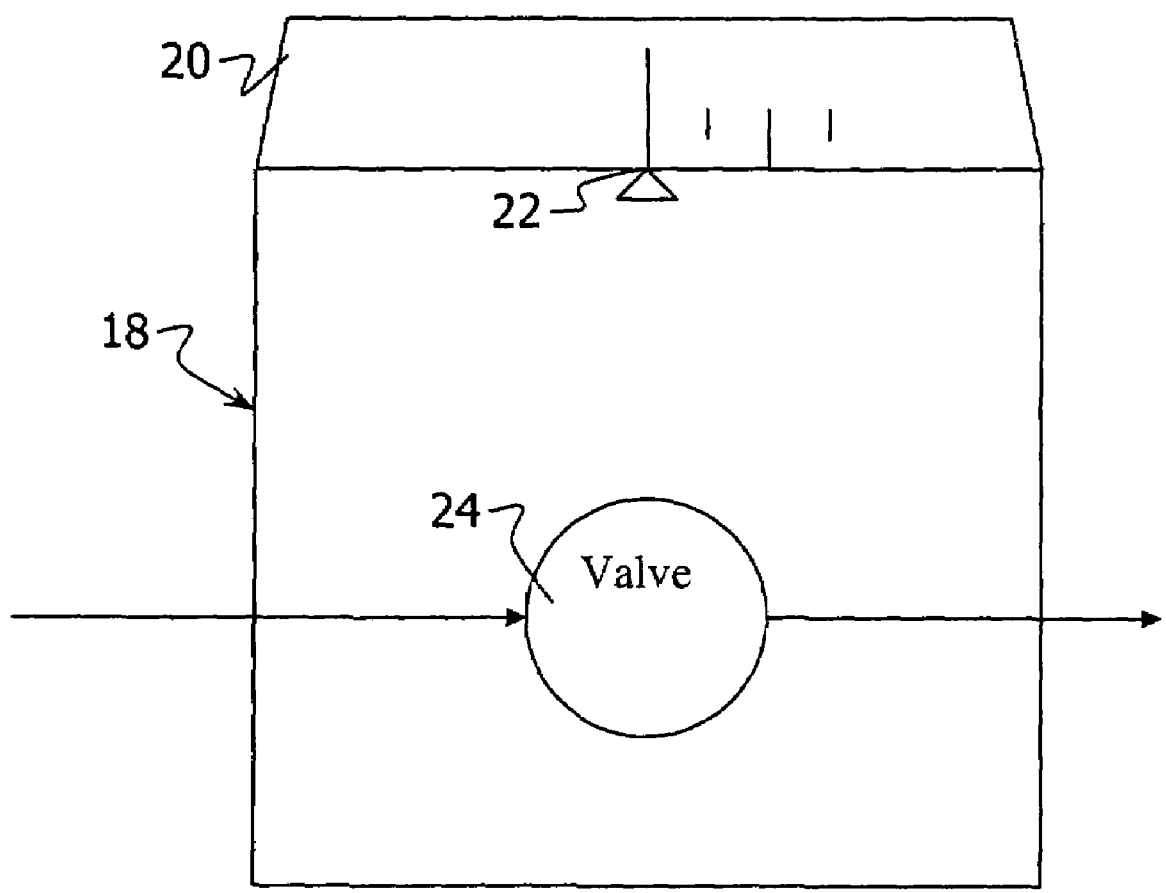
FIG. 2 is a schematic view of an assembly unit with an actuation element or handwheel for changing a setting.

FIG. 2 shows an assembly unit 18 with an actuation element or handwheel 20 for changing a setting. The setting of the assembly unit 18 determines the dispensing of at least one anesthetic. According to the invention, the actuation element or handwheel 20 has a prescribed state of operation or operation position in which no alarm is triggered, which in the example is a zero position 22. The assembly unit 18, that determines the dispensing of at least one anesthetic, may comprise an electronically driven valve assembly unit 24. Unit 24 may be a variable flow cross section portion, whose flow cross section can be set by means of the handwheel 20. In this case the prescribed state of operation, in which no alarm is triggered in case of interruption of the operating voltage, is the closed state of the mechanism with variable cross section. In this case the handwheel 20 is in the zero position 22. However, the prescribed state of operation, in which no alarm is triggered in case of interruption of the operating voltage, may be the state of the mechanism with variable flow cross section, in which the flow cross section is below a threshold value. The switches S1 and S2 are connected to the handwheel 20 as noted above. The switch (S1 and/or S2) is actuated by the actuation element or handwheel 20. The switch (S1 and/or S2) is in an open state when the actuation element or handwheel 20 is in a position in which no alarm is to be triggered (zero position 22 or below the threshold), and the switch (S1 and/or S2) is in a closed state when said actuation element or handwheel 20 is in a position in which an alarm is to be triggered.

While a specific embodiment of the invention has been shown and described in detail to illustrate the application of the principles of the invention, it will be understood that the invention may be embodied otherwise without departing from such principles.

What is claimed is:

1. An alarm in a device for dispensing volatile anesthetics, the alarm comprising:
    an alarm element;
    an operating voltage supply;
    an assembly unit that determines the dispensing of at least one anesthetic, said assembly unit having a prescribed state of operation or operation position; and
    an alarm triggering means for triggering the alarm element whenever the operating voltage is interrupted and said assembly unit is not in said prescribed state of operation or operation position.

2. A device in accordance with claim 1, wherein said assembly unit that determines the dispensing of at least one anesthetic comprises an electronically driven valve assembly unit.

3. A device in accordance with claim 2, further comprising a buffer voltage source wherein said assembly unit that determines the dispensing of at least one anesthetic comprises an actuation element or handwheel for changing a setting of said electronically driven valve assembly unit and said triggering means comprises at least one switch actuated by said actuation element or handwheel, said switch being in an open state when said actuation element or handwheel is in a position in which no alarm is to be triggered, and said switch is in a closed state when said actuation element or handwheel is in a position in which an alarm is to be triggered, said switch being integrated within a current path that connects said triggering means with the output voltage of said buffer voltage source only when the operating voltage from said operating voltage supply is interrupted.

4. A device in accordance with claim 3, wherein a microcontroller is present, which can trigger a current path for the supply of the alarm-generating component if the supply voltage is present.

5. A device in accordance with claim 3, wherein said buffer voltage source is a rechargeable battery.

6. A device in accordance with claim 3, wherein said triggering means includes a switching circuit, which is actuated by said actuation element or handwheel.

7. A device in accordance with claim 1, wherein said assembly unit that determines the dispensing of at least one anesthetic comprises a mechanism with variable flow cross section, whose flow cross section can be set by means of a handwheel.

8. A device in accordance with claim 7, wherein the prescribed state of operation, in which no alarm is triggered in case of interruption of the operating voltage, is the closed state of the mechanism with variable cross section, in which the handwheel is in a zero position.

9. A device in accordance with claim 7, wherein the prescribed state of operation, in which no alarm is triggered in case of interruption of the operating voltage, is a state of the mechanism with variable flow cross section, in which the flow cross section is below a threshold value.

10. A device in accordance with claim 1, wherein said triggering means comprises a switch to indicate the prescribed state of operation or operation position and a current path providing a current flowing from a battery to means associated said alarm element for actuating the alarm element when the switch indicates a state other than said prescribed state of operation or operation position and the absence of an operating voltage from said operating voltage supply.

11. A device for dispensing volatile anesthetics, the device comprising:
    an assembly unit that determines the dispensing of at least one anesthetic, said assembly unit having a prescribed state of operation or operation position;
    an operating voltage supply supplying a network voltage to the device;

an alarm system with an alarm element and an alarm triggering means for triggering the alarm element whenever the operating voltage is interrupted and said assembly unit is not in said prescribed state of operation or operation position.

12. A device in accordance with claim 11, wherein said assembly unit comprises an electronically driven valve assembly unit.

13. A device in accordance with claim 12, further comprising a buffer voltage source wherein said assembly unit that determines the dispensing of at least one anesthetic comprises an actuation element or handwheel for changing a setting of said electronically driven valve assembly unit and said triggering means comprises at least one switch actuated by said actuation element or handwheel, said switch being in an open state when said actuation element or handwheel is in a position in which no alarm is to be triggered, and said switch is in a closed state when said actuation element or handwheel is in a position in which an alarm is to be triggered, said switch being integrated within a current path that connects said triggering means with the output voltage of said buffer voltage source only when the operating voltage from said operating voltage supply is interrupted.

14. A device in accordance with claim 13, wherein a microcontroller is present, which can trigger a current path for the supply of the alarm-generating component if the supply voltage is present.

15. A device in accordance with claim 13, wherein said buffer voltage source is a rechargeable battery.

16. A device in accordance with claim 13, wherein said triggering means includes a switch switching circuit, which is actuated by said actuation element or handwheel.

17. A device in accordance with claim 11, wherein said assembly unit comprises a mechanism with variable flow cross section, whose flow cross section can be set by means of a handwheel.

18. A device in accordance with claim 17, wherein the prescribed state of operation, in which no alarm is triggered in case of interruption of the operating voltage, is the closed state of the mechanism with variable cross section, in which the handwheel is in a zero position.

19. A device in accordance with claim 17, wherein the prescribed state of operation, in which no alarm is triggered in case of interruption of the operating voltage, is a state of the mechanism with variable flow cross section, in which the flow cross section is below a threshold value.

20. A device in accordance with claim 11, wherein said triggering means comprises a circuit with at least one current path with a switching element.

* * * * *